US00PP26540P3

(12) United States Plant Patent
Slaughter et al.

(10) Patent No.: US PP26,540 P3
(45) Date of Patent: Mar. 29, 2016

(54) NECTARINE TREE 'BURNECTTWENTYNINE'

(50) Latin Name: *Prunus persica*
Varietal Denomination: Burnecttwentynine

(71) Applicants: John K. Slaughter, Fresno, CA (US); Timothy J. Gerdts, Kingsburg, CA (US)

(72) Inventors: John K. Slaughter, Fresno, CA (US); Timothy J. Gerdts, Kingsburg, CA (US)

(73) Assignee: THE BURCHELL NURSERY, INC., Oakdale, CA (US)

( * ) Notice: Subject to any disclaimer, the term of this patent is extended or adjusted under 35 U.S.C. 154(b) by 173 days.

(21) Appl. No.: 13/998,901

(22) Filed: Dec. 19, 2013

(65) Prior Publication Data

US 2015/0181782 P1 Jun. 25, 2015

(51) Int. Cl.
*A01H 5/08* (2006.01)

(52) U.S. Cl.
USPC ..... Plt./190

(58) Field of Classification Search
USPC ..... Plt./190
See application file for complete search history.

*Primary Examiner* — Keith Robinson
(74) *Attorney, Agent, or Firm* — Randall Danskin PS

(57) ABSTRACT

A new and distinct variety of nectarine tree, and which is denominated varietally as 'Burnecttwentynine', is described, and which further produces an attractively colored yellow-fleshed, non-melting, clingstone nectarine, which is mature for harvesting and shipment approximately June 7 to June 15 under ecological conditions prevailing in the San Joaquin Valley of central California.

1 Drawing Sheet

Botanical designation: The present invention relates to a new, novel and distinct variety of nectarine tree, *'Prunus persica'* (subspecies *nucipersica*).

Varietal denomination: 'Burnecttwentynine.'

The present variety of nectarine tree resulted from an ongoing program of fruit and nut tree breeding. The purpose of this program is to improve the commercial quality of available deciduous fruit and nut varieties, and rootstocks, by creating and releasing promising selections of *prunus, malus, punica* and *regia* species. To this end we make both controlled and hybrid cross pollinations each year in order to produce seedling populations from which improved progenies are evaluated and selected.

The seedling 'Burnecttwentynine' was originated by us from a population of seedlings grown in our experimental orchards which are located near Fowler, Calif. The seedlings, grown on their own roots, were the result of a controlled cross made in February of 2007, of the yellow-fleshed nectarine tree, 'Burnecttwentyfour' (U.S. Pat. No. 21,724), which was the pollen parent; and the yellow-fleshed seedling nectarine tree, 'J2.035' (unpatented), and which was used as the seed parent. One seedling which are identified as 'N30.022,' and which is the present variety, exhibited especially desirable characteristics, and was marked for subsequent observation. After the 2009 fruiting season, the new, present variety, was selected for advanced evaluation and repropagation.

ASEXUAL REPRODUCTION

Asexual reproduction of a new and distinct variety of nectarine tree was accomplished by budding the new nectarine tree to 'Nemaguard' Rootstock (non-patented). This was performed by us in our experimental orchard which is located near Fowler, Calif. Subsequent evaluations have shown those asexual reproductions run true to the original tree. All characteristics of the original tree, and its fruit, were established, and appear to be transmitted through succeeding asexual propagations. We have observed fruit produced by the aforementioned trees for the past 4 successive years from 15 of these trees.

SUMMARY OF THE VARIETY

'Burnecttwentynine' is a new and distinct variety of nectarine tree, which is considered of large size, and which has vigorous growth. This new nectarine tree variety is also a regular and productive bearer of relatively large, firm, acidic, yellow fleshed, and melting clingstone fruit which have good flavor and eating quality. The tree of the present variety displays a medium chilling requirement of approximately 450 hours. Still further, the present tree also produces relatively uniformly sized fruit throughout the canopy of the tree. Additionally, the fruit produced by the present tree has a very high degree of red skin coloration, a firm flesh, and further appears to have good handling and shipping qualities. The 'Burnecttwentynine' Nectarine tree bears fruit which are ripe for commercial harvesting and shipment on approximately June 7 to June 15 under the ecological conditions prevailing in the San Joaquin Valley of central California. In relative comparison to the seed parent tree 'J2.035', (unpatented) the present new variety ripens 12-15 days later. In relative comparison to the pollen parent, 'Burnecttwentyfour', the present, new variety ripens 7-10 days later. In relative comparison to the nectarine tree, 'Diamond Bright' (U.S. Pat. No. 9,495), and which is the most similar commercial variety known to the breeders at this time, the new, present variety is both larger and develops less surface russeting. Additionally, the current variety displays a more consistent fruit set from which to better select fruiting positions, and fruit numbers per tree, than that displayed by the 'Diamond Bright' nectarine tree.

BRIEF DESCRIPTION OF THE DRAWINGS

The accompanying drawing, which is provided, is a color photograph of two mature fruit in their 5$^{th}$ year, and displaying both the apical and basal aspects thereof. One mature fruit is shown, and which is dissected sagittally with a segment removed from the sutorial plane, and is further viewed from the apical perspective, so as to reveal the flesh characteristics. The external coloration of the fruit, as shown in this photograph, is sufficiently matured for harvesting and shipment.

The colors in the photograph are as nearly true as is reasonably possible in a color representation of this type. Due to chemical development, processing, and printing the fruit depicted in these photographs may or may not be accurate when compared to the actual specimen. For this reason, future color references should be made to the color plates (Royal Horticultural Society, Fourth Edition, 2001) and the other descriptions as provided hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological and botanical details of this new and distinct variety of nectarine tree, the following has been observed during the fourth fruiting season under the ecological conditions prevailing at our orchards which are located near the town of Fowler, county of Fresno, state of California. All major color code designations are by reference to The R.H.S. Colour Chart (Fourth Edition (2001)) and which is provided by The Royal Horticultural Society of Great Britain. Common color names are also occasionally used.

TREE

Size:

*Generally*.—Considered medium-large as compared to other common commercial nectarine cultivars ripening in the early season of maturity. The tree of the present variety was pruned to a height of approximately 305.0 cm to about 310.0 cm at maturity.

*Tree height*.—Approximately 300.0 cm.

*Canopy width*.—Approximately 305.0 cm.

Vigor: Considered vigorous. The present variety grew from about 190.0 cm to 205.0 cm in height during the first growing season. The new nectarine tree variety was further pruned to a height of approximately 150.0 cm during the first dormant season, and primary scaffolds were then selected for the resulting and desired tree structure.

Productivity: Productive. The fruit set varies from 4.0 to several times more than the desired crop load. The fruit set is determined, at least in part, by thinning to develop the remaining fruit into the desired market sized fruit. The number of fruit in the fruit set varies with the prevailing climatic conditions, and the cultural practices employed during the bloom period, and is therefore not distinctive of this new variety.

Fruit bearing: Regular. The resulting fruit set has been heavy, and significant thinning was necessary during the past 4 years on the previously mentioned propagated trees.

Tree form: Upright, and pruned into a vase shape.

Tree density: Considered medium dense for the variety. It has been discovered that pruning the branches from the center of the tree to obtain a resulting vase shape allows for proper air movement in the tree, and an appropriate amount of sunlight exposure so as to enhance fruit color development and the renewal of fruiting wood throughout the canopy of the tree.

Hardiness: The present tree was grown and evaluated in USDA Hardiness Zone 9.

Winter chilling requirements: The new tree requires approximately 450 hours below 7.0 degrees C. The new variety appears to be hardy under typical Central San Joaquin Valley climatic conditions.

Rooting habit and root color: Unknown. The present variety is not grown on its own roots, but on commercial root stock. Consequently this characteristic is unknown.

Time to initiate roots: Unknown. The present variety is grown on commercial root stock. Consequently this trait is not known.

TRUNK

Diameter: Approximately 17.0 cm in diameter when measured at a distance of approximately 15.24 cm above the soil level, at the end of the fourth growing season.

Bark texture: Considered moderately rough, with numerous folds of papery scarfskin being present.

Lenticels: Numerous flat, and oval lenticels are present. The lenticels range in size from approximately 4.0 to about 6.0 millimeters in width, and from about 1.0 to about 2.0 millimeters in height. It should be noted that as the cork (bark) of trees mature the lenticels become less apparent and also less abundant.

Lenticel color: Considered an Orange-Brown, (RHS Greyed-Orange Group 166 D).

Bark coloration: Variable, but it is generally considered to be gray-brown, (RHS Greyed-Orange Group 174 A).

BRANCHES

Size: Considered medium for the variety.

Diameter: Average as compared to other nectarine tree varieties. The branches have a diameter of about 9.0 centimeters when measured during the fourth year after grafting.

Flowering shoot thickness: Considered average in thickness.

Surface texture: Average, and appearing furrowed on wood which is several years old.

Crotch angles: Primary branches are considered variable between about 50 to about 55 degrees from the horizontal axis. This particular characteristic varies due to the influence of the ambient ecological conditions and cultural practices which are employed, however.

Current season shoots: Surface texture—Substantially glabrous.

Internode length: Approximately 2.4 to about 2.5 cm. This tree characteristic is highly dependent upon plant nutrition, soil quality, pruning and prevailing tree care practices.

Color of mature branches: Medium brown, (RHS Greyed-Orange 166 B).

Current seasons shoots:

*Color*.—Light green, (RHS Green Group 137 B). The color of new shoot tips is considered a bright and shiny green (RHS Green Group 137 A).

LEAVES

Size: Considered medium for the species. Leaf measurements have been taken from vigorous, upright, current-season growth, at approximately the mid-shoot.

Leaf length: Approximately 128.0 to about 165.0 millimeters.

Leaf width: Approximately 34.0 to about 37.0 millimeters.

Leaf base shape: Slightly oblique relative to the leaf longitudinal axis.

Leaf form: Lancelolate.

Leaf tip form: Beaked.

Leaf color:

*Upper surface*.—Dark green, (approximately RHS Green Group 137 B).

Leaf texture: Both the upper and lower leaf surfaces are glabrous.

Leaf color:

*Lower surface*.—Medium green, (RHS Green Group 146 B).

Leaf venation: Pinnately veined.

Mid-vein:

*Color*.—Light yellow green, (RHS Yellow-Green Group 150 D).

Leaf margins: Slightly undulating.

*Form*.—Considered crenate, occasionally doubly crenate.

*Uniformity*.—Considered generally uniform.

Leaf petioles:

*Size*.—Considered long for the species.

*Length*.—About 7.0 to about 9.0 mm.

*Diameter*.—About 1.5 to about 2.0 mm.

*Color*.—Pale green, (RHS Yellow-Green Group 150 B).

Leaf petiole strength: Durable for the species until senescence.

Leaf petiole texture: Glabrous.

Leaf glands:

*Size*.—About 1.0 mm in height, and about 2.0 mm in width.

*Number*.—Generally one per side, occasionally two per side.

*Type*.—Reniform, considered reasonably unappressed to the petiole margin, and moderately small. The glands on more mature leaves are occasionally senescent.

*Color*.—Orange brown, (RHS Greyed-Green Group N189 B).

Leaf stipules:

*Size*.—Medium for the variety.

*Length*.—Approximately 5.0 to 6.0 mm.

*Width*.—Approximately 1.0 to 1.5 mm.

*Number*.—Typically 2 per leaf bud, and up to 6 per shoot tip.

*Form*.—Lanceolate in form, and having a serrated margin.

*Color*.—Green, (RHS Green Group 141 A) when young, but graduating to a brown color, (RHS Greyed-Orange group 177 B) with advancing senescence. The stipules are considered to be early deciduous.

FLOWER BUDS

Flower buds:

*Generally*.—The floral buds, depending upon the stage of development, are approximately 8.0 millimeters wide; and about 12.0 millimeters long; conic in form; and slightly appressed relative to the bearing shoot.

Flower buds:

*Color*.—The bud scales are reddish-brown, (approximately RHS Greyed Red Group 178 A). The buds are considered hardy under typical central San Joaquin Valley climatic conditions.

Hardiness: No winter injury has been noted during the last several years of evaluation in the central San Joaquin Valley. The current variety has not been intentionally subjected to drought or heat stress, and therefore this information is not available. The current variety is considered to be a lower chilling requirement variety for the region where it is currently being grown. It is possible for this variety to experience frost damage on either the developing flowers or small fruit due to the early initiation of the blooming period, and the further exposure of the flowers, or developing fruit to the damaging temperatures which are experienced during the late winter months and after the first bloom.

FLOWERS

Blooming time: Considered early to mid-season in relative comparison to other commercial nectarine cultivars grown in the central San Joaquin Valley.

Date of first bloom: Feb. 19, 2013. Date of full bloom was observed on Feb. 29, 2013. The date of first bloom varies slightly with the prevailing climatic conditions, and cultural practices which are employed.

Duration of bloom: Approximately 10 days. This characteristic varies slightly with the prevailing climatic conditions.

Flower class: Perfect, complete and perigynous.

Flower type: The variety is considered to have a showy type flower.

Flower size: The flower diameter at full bloom is approximately 38.0 to about 42.0 millimeters.

Bloom quantity: Considered very abundant.

Flower bud density: Generally, very dense.

Flower bud frequency: Normally 2 flower buds appear per node. Occasionally 3 buds per node may be observed.

Petal size:

*Generally*.—Considered medium large for the species.

*Length*.—Approximately 18.0 to about 20.0 millimeters.

*Width*.—Approximately 16.0 to about 18.0 millimeters.

Petal form: Rotund to slightly ovate.

Petal count: Generally 5. Occasionally individual flower pedal counts are doubled.

Petal texture: Both the upper and lower surfaces of the petal are glabrous.

Petal color: Light pink, (RHS Red-Purple Group 62 B) to a medium pink, (RHS Red-Purple Group N57 C).

Fragrance: Slight.

Petal claw:

*Form*.—The claw is considered truncate in shape, and has a large size when compared to other varieties.

*Length*.—Approximately 11.0 to about 13.0 millimeters.

*Width*.—Approximately 10.0 to about 11.0 millimeters.

Petal margins: Generally considered variable, from nearly smooth, to moderately undulate.

Petal apex: Generally—The petal apices generally appear entire.

Flower pedicel:

*Length*.—Considered medium-long, and having an average length of approximately 5.0 to about 6.0 millimeters.

*Diameter*.—Considered average, approximately 2.0 millimeters.

*Color*.—A pale green, (RHS Greyed-Green Group 194 B).

Flower pedicel strength: Tenacious, but considered average for the species.

Flower pedicel texture: Glabrous.

Floral nectaries:

*Color*.—An orange brown, (RHS Greyed-Orange Group N172 B).

Calyx:

*Surface texture*.—Generally glabrous.

*Color*.—A dull red, (approximately RHS Greyed-Orange Group 176 A).

Sepals:

*Surface texture*.—The upper surface has a short, fine, pubescent texture. The lower surface is glabrous.

*Number*.—Nearly always 5.

*Size*.—Average, and ovate in form.

*Sepal length*.—Approximately 4.0 mm to 5.0 mm.

*Sepal width*.—Approximately 3.5 mm to 5.0 mm.

*Sepal shape*.—A single entire lobe. Ovatum to nearly round.

*Color*.—A dark reddish purple, (approximately RHS Greyed-Purple Group 183 B).

Anthers:

*Generally*.—Large in size.

*Color*.—Red to reddish purple, (approximately RHS Greyed-Purple Group 187 C) prior to dehiscence.

Pollen production: Pollen is abundant, and has a yellow color, (approximately RHS Yellow Group 11 A).

Fertility: Self-fertile.

Filaments:

*Size*.—Variable in length, approximately 15.0 to about 18.0 millimeters in length.

*Color*.—Considered a pale pink, (RHS Red-Purple Group 65 C).

Stamen position: At flower maturity the Stamens grow to be superior to the petals.

Pistil:

*Number*.—Normally 1, very rarely 2.

*Generally*.—Average in size.

*Length*.—Approximately 16.0 to about 19.0 millimeters including the ovary.

*Color*.—Considered a very pale green, (approximately RHS Yellow-Green Group 145 C).

*Surface texture*.—The variety has a long glabrous pistil.

Stigma position: Generally the Stigma is superior to the anthers by about 1.0 to about 2.0 mm. Ovary surface texture and color—Presently unknown.

FRUIT

Maturity when described: Firm ripe condition (shipping ripe).

*Date of first picking*.—Jun. 7, 2013.

*Date of last picking*.—Jun. 15, 2013. The date of harvest varies slightly with the prevailing climatic conditions.

Size:

*Generally*.—Considered large, and uniform.

Average cheek diameter: Approximately 70.0 to about 72.0 millimeters.

Average axial diameter: Approximately 72.0 to about 74.0 millimeters.

Typical weight: Approximately 230.0 grams. This characteristic is highly dependent upon the cultural practices employed.

Fruit form:

*Generally*.—Rounded to slightly oblate. The fruit of the new variety can exhibit an extended and prominent suture along both hemispheres. A mucron tip at the pistil end of the fruit is absent.

Fruit suture: Shallow, and extending from the mid-equatorial region to the apex. No apparent callousing or stitching exists along the suture line.

Suture:

*Color*.—The background color appears to be an orange yellow, (approximately RHS Orange Group N25 D), with a predominant red coloration, (approximately RHS Red Group 46).

Ventral surface:

*Form*.—Full.

Apex:

*Shape*.—Rounded.

Base:

*Form*.—Retuse.

Stem cavity: Rounded and relatively shallow. The average depth of the stem cavity is about 18.0 mm. The average width of the stem cavity is about 2.00 mm.

Fruit skin:

*Thickness*.—Considered medium in thickness, and tenacious to the flesh.

*Surface texture*.—Glabrous.

*Taste*.—A slight astringency can be detected.

*Tendency to crack*.—Cracking has not been observed. Russeting has not been observed to date.

Color:

*Blush color*.—The blush color is variable from a medium red, (approximately RHS Red Group 44 A) to a dark red, (approximately RHS Red Group 46 A). The observed blush color ranges from 85% to about 95% of the fruit surface depending upon the sunlight exposure, and the prevailing climate, canopy development and growing conditions.

Ground color: Generally a deep yellow, (approximately RHS Orange Group N25 D).

Fruit glossiness: Considered medium to strong.

Fruit stem: Moderate in length, approximately 7.0 to about 9.0 millimeters.

*Diameter*.—Approximately 2.0 to about 2.5 millimeters.

*Color*.—Light tan, ((approximately) RHS Greyed-Orange Group 164 D).

Flesh:

*Ripens*.—Evenly.

*Texture*.—Firm, and dense. Overall the fruit is considered firm melting.

*Fibers*.—Few, small, and tender ones are apparent.

*Aroma*.—Slight.

*Eating quality*.—Considered good.

*Flavor*.—Considered sweet, acidic, and pleasant.

*Juice*.—Moderate.

*Brix*.—About 13.5 degrees. This characteristic varies slightly with the number of fruit per tree; the prevailing cultural practices; and the surrounding climatic conditions.

*Flesh color*.—Yellow, (approximately RHS Yellow-Orange Group 17 C).

Fruit acidity as expressed as titratabe acidity in meq per 100 ml: Unknown.

STONE

Type: Clingstone.

Size: Considered medium large for the variety. The stone size varies with the resulting crop load, and tree vigor.

Length: Average, about 27.0 to about 31.0 millimeters.

Width: Average, about 22.0 to about 25.0 millimeters.

Diameter: Average, about 17.0 to about 22.0 millimeters.

Stone form: Obovoid.

Stone base: The stone is relatively uniform in its margin relative to the stone's vertical axis.

Apex:

*Shape*.—The stone apex is relatively smooth with a significant recess being observed near the apex, and extending approximately 5.0 mm along the dorsal edge thereof.

Stone surface:

*Surface texture*.—Substantial pitting is evident, in general, from the base and past the equatorial plane. Grooving is usually observed along the pit margin near the tip, and on the ventral side.

*Ridges*.—The surface texture is generally rounded.

*Ventral edge*.—Width — Considered medium, and having a dimension of approximately 4.0 to about 7.0 millimeters when measured at the mid-suture.

*Dorsal edge*.—Shape — Full, heavily grooved, and having relatively smooth edges.

Stone color: The color of the dry stone is tan (Greyed-Orange Group approximately RHS 172 B). The stone as seen in the photo as provided with the present application is freshly exposed and can occasionally exhibit darkening hues which are the result of oxidation.

Tendency to split: Rarely splits have been observed.

Kernel:

*Generally*.—The kernel, when the fruit is picking ripe, is not completely mature when compared to kernels of fruit varieties with a greater development period.

*Form*.—Considered ovoid.

*Surface texture*.—Pubescent.

*Color*.—Considered to be a pale tan (Greyed-Yellow Group 162 D).

Use: The subject variety 'Burnecttwentynine' is considered to be a Nectarine tree which matures early in the season, and which further produces fruit, which are considered firm, attractively colored, flavorful and which are useful for both local and long distance shipping.

Keeping quality: Excellent. Fruit has stored well for up to 30 days after harvest at 1.0 degree Celsius.

Shipping quality: Good. The fruit of the new nectarine tree variety showed minimal bruising of the flesh, or skin damage, after being subjected to normal harvest and packing procedures.

Resistance to insects and disease: No particular susceptibilities were noted. The present variety has not been tested to expose or detect any susceptibilities or resistances to any known plant and/or fruit diseases. No new tests or observations have been made subsequent to the filing of the present patent application.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by Plant Letters Patent is:

1. A new distinct variety of nectarine tree, substantially as illustrated and described, and which is characterized principally as to novelty by producing an attractively colored, yellow-fleshed, firm-melting, acidic clingstone nectarine which is mature for harvesting and shipment approximately June 7 to June 15 under the ecological conditions prevailing in the San Joaquin Valley of central California.

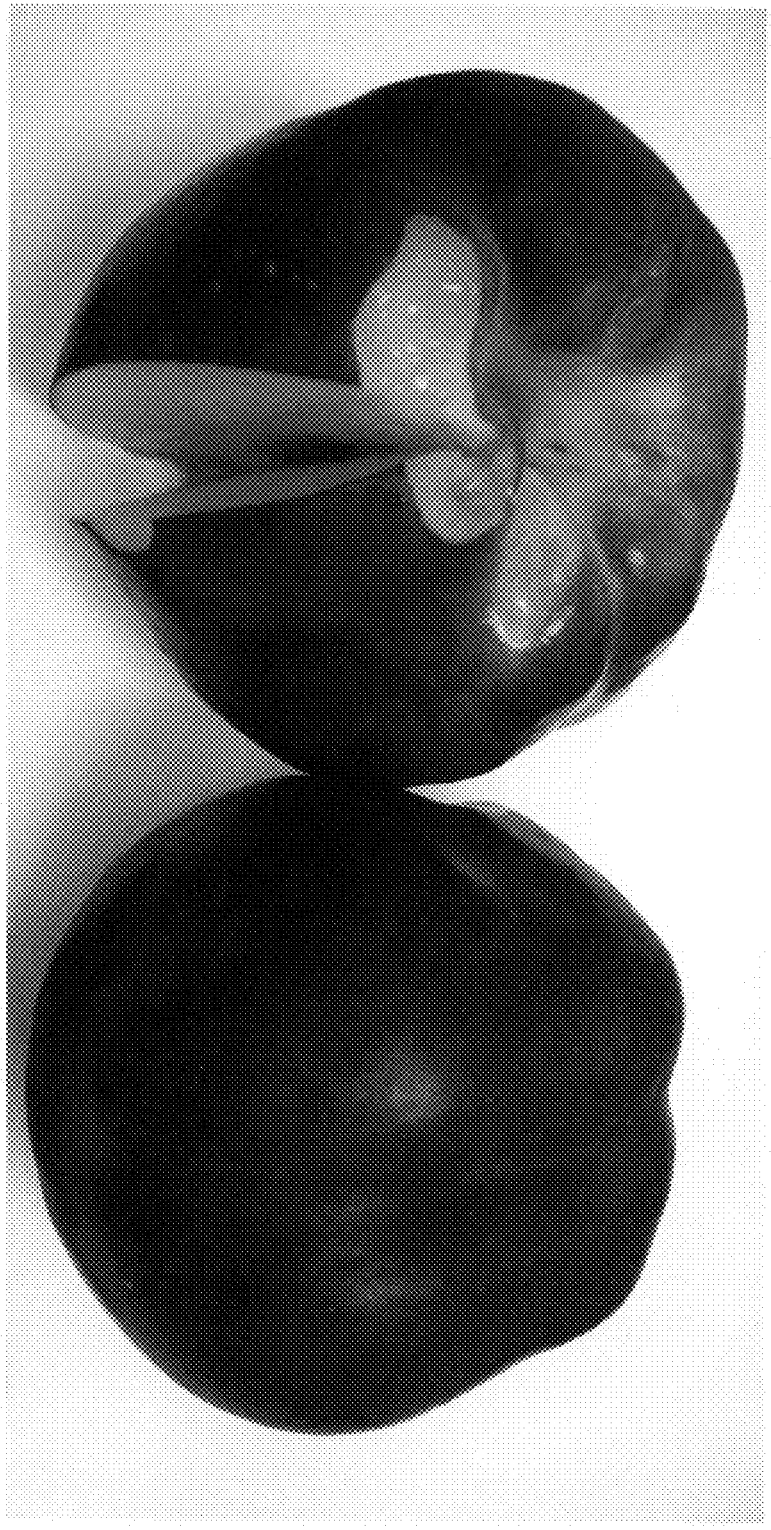

* * * * *